(12) United States Patent
Fischell et al.

(10) Patent No.: US 9,849,302 B1
(45) Date of Patent: Dec. 26, 2017

(54) THREE-COIL MAGNETIC PULSATIONS SYSTEM FOR THE TREATMENT OF FOOT PAIN

(71) Applicant: ZYGOOD LLC, Dayton, MD (US)

(72) Inventors: Susan R. Fischell, Dayton, MD (US); Robert E. Fischell, Dayton, MD (US)

(73) Assignee: Zygood, LLC, Dayton, MD (US)

( * ) Notice: Subject to any disclaimer, the term of this patent is extended or adjusted under 35 U.S.C. 154(b) by 0 days.

(21) Appl. No.: 15/378,695

(22) Filed: Dec. 14, 2016

Related U.S. Application Data

(63) Continuation-in-part of application No. 14/921,452, filed on Oct. 23, 2015, now Pat. No. 9,550,067.

(51) Int. Cl.
| | |
|---|---|
| *A61N 2/02* | (2006.01) |
| *A61N 2/00* | (2006.01) |
| *A43B 7/00* | (2006.01) |
| *A43B 1/00* | (2006.01) |

(52) U.S. Cl.
CPC ............ *A61N 2/008* (2013.01); *A43B 1/0081* (2013.01); *A43B 7/00* (2013.01); *A61N 2/02* (2013.01)

(58) Field of Classification Search
CPC ...... A61N 2/00–2/12; A43B 1/00–1/14; A43B 1/0054; A43B 3/00–3/30; A43B 5/00–5/185; A43B 7/00–7/38; A43B 9/00–9/20
See application file for complete search history.

(56) References Cited

U.S. PATENT DOCUMENTS

| | | | | |
|---|---|---|---|---|
| 7,520,849 | B1 * | 4/2009 | Simon ...................... | A61N 2/02 600/14 |
| 2011/0021863 | A1 * | 1/2011 | Burnett .................... | A61N 2/02 600/14 |
| 2012/0316382 | A1 * | 12/2012 | Edwards .................. | A61N 2/06 600/15 |
| 2013/0030239 | A1 * | 1/2013 | Weyh ...................... | A61N 2/006 600/14 |
| 2014/0024882 | A1 * | 1/2014 | Chornenky .............. | A61N 1/40 600/14 |
| 2014/0221726 | A1 * | 8/2014 | Pilla ..................... | A61N 1/36014 600/14 |
| 2015/0360045 | A1 * | 12/2015 | Fischell .................. | A61N 2/02 600/14 |

* cited by examiner

*Primary Examiner* — Thaddeus Cox
(74) *Attorney, Agent, or Firm* — Rosenberg, Klein & Lee

(57) ABSTRACT

A magnetic coil system for the treatment of foot pain which has an electrical pulse generator sequentially connected to three separate magnetic coils that have been placed around that patient's foot. The magnetic coil system consisting of one bottom coil, one coil on top of the foot and a third coil that is situated around the back of the foot and the bottom of the ankle. The three coils being separately and sequentially activated by the electrical pulse generator. The treatment of plantar fasciitis being accomplished by the activation of a series of intense magnetic pulsations using only the bottom coil.

12 Claims, 3 Drawing Sheets

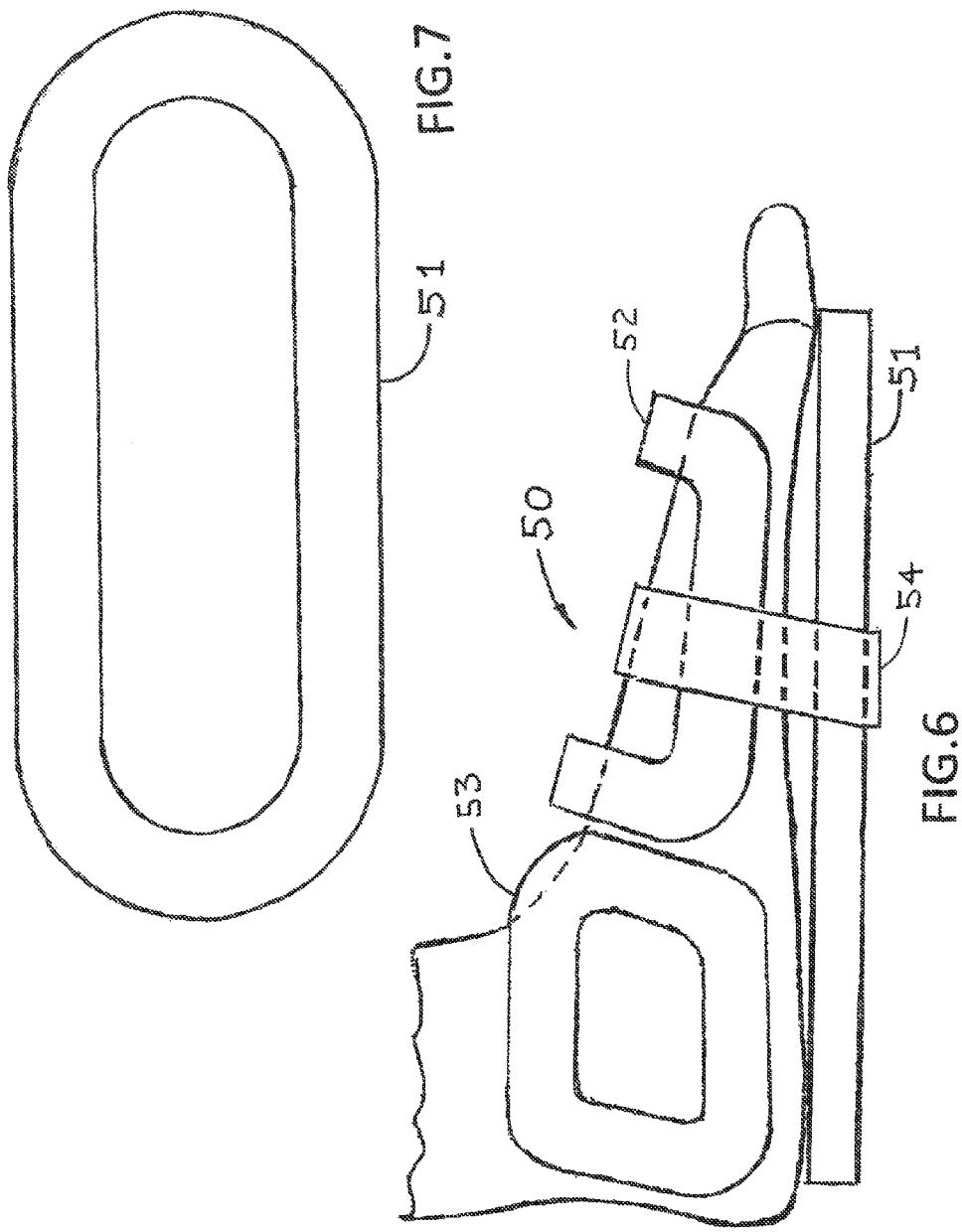

THREE-COIL MAGNETIC PULSATIONS SYSTEM FOR THE TREATMENT OF FOOT PAIN

REFERENCE TO RELATED APPLICATION

This Application is being filed as a Continuation-in-Part of application Ser. No. 14/921,452, filed 23 Oct. 2015, now U.S. Pat. No. 9,550,067.

FIELD OF USE

This invention is in the field of methods and devices to be used by human subjects to decrease or eliminate foot pain without the use of ingested or injected drugs.

BACKGROUND OF THE INVENTION

It is well known that there are literally millions of patients throughout the world who suffer pain in various parts of their bodies. Three of the most frequent sites for pain are: (1) foot pain caused by chemotherapy or diabetic neuropathy; (2) shoulder pain often resulting from a tear or inflammation of the rotator cuff; and (3) lower back pain caused by a large variety of medical problems, particularly associated with the spine and the nerves surrounding the vertebrae. Although there are many pain medications to reduce the level of pain experienced by such patients, these drugs often are not sufficiently palliative and they typically can cause serious side effects.

One early invention to utilize magnetic fields to treat pain is described by Robert R, Holcomb in International Publication Number: WO 91/15263. The invention described in that document consists of four magnetic coils that are placed in the back of a chair or under a table where the patient's back would be exposed to the magnetic field. A DC current is placed through the four coils which results in an unchanging magnetic field to be experienced by the patient.

In U.S. Pat. No. 6,402,678, Robert E. Fischell, et al describe a device to be placed on the head which can eliminate or reduce the pain of migraine headaches by the application of a series of intense magnetic pulses. This device was approved by the US FDA on May 22, 2014 and is currently in use to treat patients with migraine headaches. The Fischell, et al migraine treatment device operates by charging capacitors to a high voltage and then discharging them into a magnetic coil to create a magnetic pulse that reaches a peak intensity of about 0.8 Tesla in less than 200 microseconds. By Faraday's law, this changing magnetic field intensity creates an electrical pulse within the skull that has been shown to eliminate migraine headaches. Because it takes about 45 seconds to charge the condensers from a battery within this Transcranial Magnetic Stimulation (TMS) device, the rate of applying magnetic pulses to the brain is extremely slow; i. e., typically about one pulse in about one minute. Even at that, the time rate of change of the magnetic field within the brain results in an electrical current in some neurons which eliminates most migraine headaches. However, the application of more pulses per unit time and at a higher magnetic field intensity with specially shaped magnetic coils could result in a more effective treatment for the relief of pain from other parts of the human body such as the feet for patients who suffer from diabetic neuropathy or cancer chemotherapy.

An existing system that is currently available to treat lower back pain is called TENS which is an acronym for Transcutaneous Electrical Nerve Stimulator. This device has two adhesive covered electrodes that are pasted onto the skin along the lower back. The device can then be turned on and adjusted so that the pain in the skin is acceptable while some electrical pulses enter the body in the vicinity of the spine where they can provide some relief for lower back pain. However, it would be highly advantageous to use a system that could provide higher intensity electrical pulses much deeper into the body without causing any skin pain. That can be accomplished with TransCutaneous Magnetic Stimulation or TCMS as described herein.

There is one issued patent and three patent applications by Donald Burnett et al namely U.S. Pat. No. 6,701,185 (the '185 patent), and the patent publications US2003/0158585 (the '585 publication), US2004/0210254 (the '254 publication) and US2012/0302821 (the '821 publication). The inventions described in the Burnett et al patent and publications all have a consistent design for the use of magnetic pulsations for the treatment of pain, namely, comparatively small wire coils with all wires being in circular form and placed against the skin of the foot or wrapped around the knee or elbow with the use of comparatively low electrical currents. Specifically, this prior art has the following numbers of generally circular or curved magnetic coils: the '185 reference 6 coils; the '585 reference, 10 coils; the '254 reference, 9 coils; and the '821 reference, 30 coils. Not even one of these 49 coil designs has even one straight wire section for placement anywhere on a human body. The Burnett et al references describe 23 different coil designs placed against the side of the foot and three different designs that are needles placed against the side of the foot. At no point in any of these prior art documents is there any design surrounding the foot and no Burnett et al design even closely approximates a shoe-shaped coil that is placed around the foot which is undoubtedly the optimum configuration for the application of magnetic pulsations to treat foot pain. The Burnett et al references also do not describe any combination of three coils to surround the foot and lower ankle to relieve pain by the sequential application of intense magnetic pulsations from each of those three coils.

SUMMARY OF THE INVENTION

The present invention is a means and method to apply TransCutaneous Magnetic Stimulation (TCMS) to relieve pain in the foot of a human subject without the use of an analgesic drug. The TCMS system consists of an electrical pulse generator that would typically be plugged into a wall electrical socket and would provide by means of an attached magnetic coil repeated magnetic pulses into the entire foot and typically up into the patient's ankle. This type of coil could be extended further around the ankle to reduce pain in both the foot and the upper ankle. This unique design for a magnetic coil in the general shape of a shoe would be particularly advantageous for those patients who suffer foot and ankle pain resulting from extensive cancer chemotherapy or from diabetic neuropathy or the pain experienced at the bottom region of the foot which is called plantalgia that is caused by tissue inflammation at the bottom of the foot, which inflammation is called plantar fasciitis.

The optimum design for the coil for treating foot and ankle pain is to have the coil in the general shape of a shoe. This shape provides the greatest magnetic field onto the foot and ankle while using a minimum length of the wire and a minimum coil diameter so as to obtain the highest peak magnetic pulsations while minimizing the electrical voltage, electrical current and electrical power that is needed to treat the pain in that region. Furthermore, by having straight wires under the foot where that foot is generally flat and also having an increasing area of each single turn of wire in the coil as one proceeds from the toe toward the ankle, this novel design provides the highest possible magnetic field strength with the least electrical current and power and also the least coil heating during the pain treatment session. Still further, by having a thick, padded foam rubber or equivalent lining within the foot and ankle coil, fewer different size coils are needed to treat the variety of sizes of human feet that would be using this coil system for the treatment of foot and ankle pain. Still further, this soft inner lining for the foot and ankle coil system would provide a greater degree of comfort for the patients while using this device to reduce foot and ankle pain. Still further, an adjustable tilt platform could be used to adjust the angle of the shoe-shaped coil relative to the floor to optimize the comfort of the patient as he/she is sitting in a chair for an extended period of time to be treated for foot pain.

One problem that is associated with a coil in the general shape of a shoe or sneaker is that it is sometimes difficult for a patient with severe foot pain to place his/her foot into such a coil. Since there are many of those patients, an alternative design would be to have as many as three coils that surround the foot and lower ankle. For this design, there would be one coil placed beneath the foot, one coil on top of the foot and a third coil that surrounds the back of the foot and a lower part of the ankle. Each one of the three coils would be separately placed and secured onto the foot with a means such as a Velcro fastener that would hold that particular coil against the patient's foot.

Another advantage of having three coils to surround the foot with each coil being separately activated is that this design provides a much increased magnetic field pulse amplitude to obtain improved pain relief in the foot and lower ankle. The design of one coil that surrounds the entire foot and lower ankle has a much higher electrical resistance and inductive reactance as compared to a coil that surrounds only ⅓ of the foot. Therefore, higher magnetic field intensities can be accomplished if each of three separate coils is used successively to create the highest possible magnetic pulse intensity.

The electrical pulse generator would typically get its power by being plugged into a wall electrical socket. However, the use of a primary or rechargeable battery for the electrical pulse generator is certainly possible.

The waveform for treatment would be a magnetic pulse with a rise time between 10 and 500 microseconds. A pulse length of approximately 160±25 microseconds would be ideal for this purpose. The stimulation pulse rate would optimally be at a rate between 0.05 Hz and 10 Hz with an optimum pulse period being a pulse every 2 seconds to a pulse every 10 seconds which is essentially 0.1 Hz to 0.5 Hz. It is also conceived that the wave form could be approximately half of one sine wave or a square wave to optimize the relief of pain. The peak amplitude for the magnetic pulses at the patient's skin should be at least 0.3 Tesla with an optimum magnetic pulse strength at the skin being between 0.8 and 3.0 Tesla. To accomplish this level of peak magnetic pulse intensity, it would be typical to have a peak electrical current in the coil that could be as small as 500 Amperes or as strong as 10,000 Amperes. The peak pulse voltage to accomplish these intense levels of electrical current could be between 500 and 10,000 Volts.

Thus one object of the present invention is to provide a means and method to treat foot and/or foot and ankle pain of a human patient by the application of high intensity magnetic pulsations through the patient's skin at that location where those magnetic pulsations create subcutaneous electrical current pulses that reduce the level of pain in the foot or in both the foot and the ankle.

Another object of this invention is to optimize the size and shape of the magnetic coil to best fit that patient's foot and/or foot and ankle.

Still another object of this invention is a method to diminish the pain caused by diabetic neuropathy in the foot and/or foot and ankle.

Still another object of this invention is a method to diminish the pain caused by cancer chemotherapy in the foot and/or foot and ankle.

Still another object of this invention is a method to diminish the pain within the tissue at the bottom of the foot, which pain is called plantalgia.

Still another object of this invention is to have the magnetic coil in the general shape of a shoe which provides a magnetic field onto the entire volume of the patient's foot and ankle.

Still another object of this invention is to have straight wire sections at the bottom of the shoe-shaped coil for optimum creation of the magnetic field within the patient's foot and for optimum comfort for the patient during the extended time period required for the treatment of foot pain.

Still another object of this invention is to have a thick padding within the coil that surrounds the foot so that patients with at least three different shoe sizes could use the same coil system.

Still another object of this invention is to have a collection of three separate coils that surround the foot and lower ankle with each coil being separately fastened to the foot before each is energized with electric current to produce the appropriate magnetic pulsations to alleviate pain.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 6 illustrates a collection of three coils that surround the foot and lower ankle for the application of intense magnetic pulsations from each coil.

FIG. 7 is a plan view of the foot coil for placement under a patient's foot for the treatment of foot pain.

DETAILED DESCRIPTION OF THE INVENTION

Figure 1:
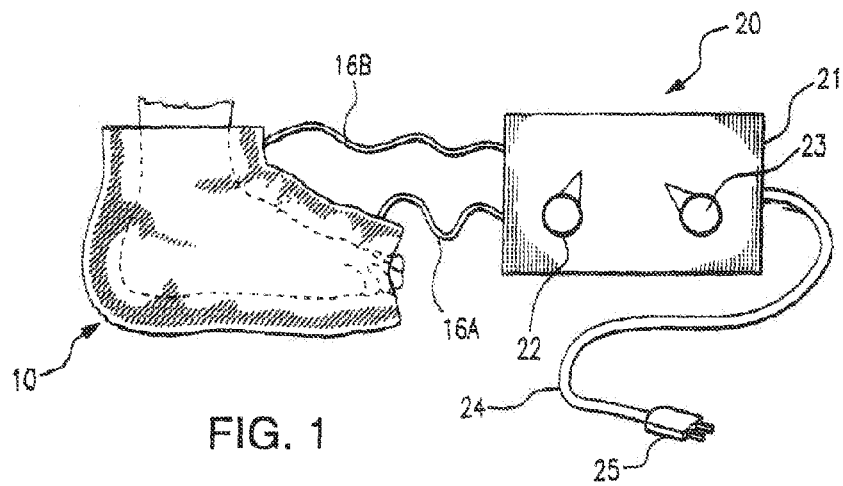
FIG. 1 illustrates a magnetic coil placed around the foot and ankle of a patient for the treatment of foot and/or foot and ankle pain, the coil being connected to an electrical pulse generator that is plugged into a wall socket.

FIG. 1 illustrates a TransCutaneous Magnetic Stimulator (TCMS) magnetic coil system 10 connected to an electrical pulse generator system 20 for the treatment of foot and/or foot and ankle pain. The electrical pulse generator system 20 receives its electrical power through the wire 24 that is connected to the plug 25 that would be placed into a conventional electrical socket (not shown). The electrical pulse generator system 20 would be capable of providing the pulses of electrical current that go through the foot coil 10 for the creation of intense magnetic pulsations within the coil 10 for the treatment of foot and ankle pain.

Figure 2:
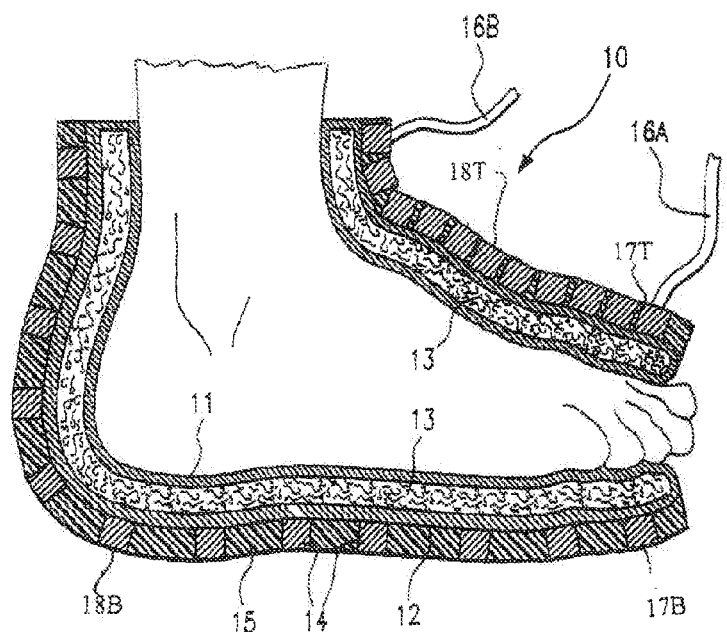
FIG. 2 is a cross section of a magnetic coil placed around the foot and ankle of a patient for the treatment of foot pain or for the treatment of foot and ankle pain.

Although the optimum electrical pulse generator system 20 would get its power as shown in FIG. 1, it is also conceived that the electrical pulse generator 21 could get its power from a primary or a rechargeable battery. The dials 22 and 23 on the face of the electrical pulse generator 21 would be used to adjust the pulse frequency and pulse amplitude for the electrical current pulses created by the electrical pulse generator system 20 to create the magnetic pulses that would be delivered by the magnetic coil system 10. These electrical current pulses would be delivered to the magnetic coil system 10 by means of the wires 16A and 16B as shown in FIGS. 1 and 2. Electrical pulses with a pulse amplitude as high as 10,000 Amperes could be generated by the pulse generator 21. The lowest pulse amplitude would be at least 500 Amperes to obtain the desired intensity for the magnetic pulses to be delivered by the magnetic coil system 10, the optimum electrical current being between 800 and 1,200 Amperes. It should also be understood that the pulse generator system could also have separate controls to control other pulse variables such as the pulse duration, the pulse amplitude, the number of pulses to be used for a treatment and the time between each pulse. Of great importance is to utilize a wire size that will not create undue heating of the coil 10 during a treatment for pain. To that end, it is optimal to utilize copper or aluminum wire sizes that lie between #2 AWG and #8 AWG. These wire sizes are required to keep the heating effect from the electrical pulses through the coil from reaching too high a temperature for a typical 10 to 30 minute treatment time period for each patient. This is in contradistinction to the Burnett et al '185 patent that preferably utilizes #12 AWG coil wire size which would result in the creation of excessive coil heating for the levels of magnetic field intensity that are required for obtaining significant pain relief. The Burnett et al '185 patent also describes the use of wire sizes from as low as #10 AWG to as high as #20 AWG, none of which would be suitable for the maintenance of a reasonable coil temperature when using the high levels of electrical current as required for effective treatment of foot pain.

The electrical pulse generator system 20 would include conventional circuitry to generate a pulse waveform, a sinusoidal wave form, a square wave waveform or any other pulse wave form that is found to be effective for stimulation of nerves. The frequency of the pulses could be anything between 0.1 Hz and 10 Hz with an optimum pulse rate being approximately 0.15 to 1.0 Hz. The pulse amplitude generated by the magnetic coil 10 could be anything between 0.3 Tesla and 5.0 Tesla with an optimum magnetic pulse peak intensity being between approximately 0.5 and 3.0 Tesla. None of the Burnett et al publications or his single patent describes the level of magnetic field strength that is required to provide foot and ankle pain relief for a human subject. When pulses are used for TCMS, the pulse rise time could be between 10 and 500 microseconds with an optimum pulse rise time being approximately 160±25 microseconds. The Burnett et al '185 patent suggests the use of pulse durations as high as 200,000 microseconds (i. e., 200 milliseconds) which would be completely unacceptable to generate the high rate of change of the magnetic pulses that is required to obtain sufficiently high electrical currents within the foot and ankle to generate by Faraday's law an adequate electrical current pulse for the electrically conducting human tissue within the foot and ankle to eliminate pain.

FIG. 2 is a cross section of the magnetic coil system 10 placed around the foot and ankle of a patient who suffers from foot pain or foot and ankle pain. This pain would typically be caused by extensive cancer chemotherapy or would be a result of diabetic neuropathy or from plantalgia. The inner lining 11 of the magnetic coil system 10 would be situated closely around the patient's foot and ankle. Surrounding the inner lining 11 would be a soft elastic material 13 that is contained within the inner lining 11 and the outer covering 12. It should be noted that (as shown in FIG. 2) the inner lining 11 and outer covering 12 could in fact be formed from one piece of material such as leather or a plastic material such as Nylon. The soft elastic material 13 may be porous and could be formed from a material such as cotton or foam rubber or any other material that would make it moderately easy for the patient to place his/her foot within the magnetic coil system 10. It is also conceived to have the patient wear a tight fitting and somewhat slippery sock when placing his/her foot into the magnetic coil system 10. That would be especially needed if the same magnetic coil system 10 is made available in a commercial medical facility for many different patients.

A great advantage of the design shown in FIG. 2 is that patients with as many as three different shoe sizes could fit into the coil system 10 shown in FIG. 2. For example, if the maximum foot size that could fit into the coil system 10 of FIG. 2 was a ten, then this design could also accommodate sizes eight and nine without losing any significant strength of the magnetic field experienced by the patient who would use that shoe-shaped coil system. It is also expected that the shoe sizes that could be used with the coil system 10 could go from as small as a woman's size four to as large as a man's size fifteen. In none of the Burnett et al publications or patent is there any mention of a coil in the form of a shoe into which a patient suffering from foot and ankle pain could place his/her foot. Only this shoe-shaped coil has the appropriate shape for treating foot pain.

Figure 3:
FIG. 3 illustrates cross sections of various wires that could be used for the magnetic coil.

FIG. 2 also shows the cross section of square wire magnetic coil 14 that is wrapped around the outer covering 12. A total of 12 turns of the magnetic coil 14 are shown in FIG. 2. Any number of turns between 4 and 30 could be used for such a magnetic coil 14 with an optimum number of turns being approximately 14±7 turns. It should also be understood that the wire of the coil 14 would be insulated on its exterior and would have a cross section that could be of any one of several different shapes as shown in FIG. 3. Surrounding the magnetic coil 14 would be a thin coil covering member 15 that could be formed from a plastic material or from certain cloth materials. It should also be understood that the wires 14 could be adhesively attached to the outer layer 12 or there could be a plastic fill material 15 situated between each turn of the wires of the magnetic coil 14. FIG. 2 also shows the wires 16A and 16B which are attached to the electrical pulse generator 20 as shown in FIG. 1.

Of great importance to the design of an effective coil system 10 for the treatment of foot and ankle pain, is the shape of that coil 10 which is generally in the novel shape of a shoe such as a typical sneaker. Specifically, the bottom coil wires 17B and 18B at the bottom of the shoe-shaped coil 10 are essentially straight wires situated transverse to the length of the foot and they are as close as reasonably possible to the bottom of a human foot. This unique design for the coil 10 provides the maximum magnetic field intensity onto the bottom tissue of the foot that especially optimizes the treatment of pain for a condition such as plantalgia. The top portions of the coil 10, namely the top curved coil wires 17T and 18T have a curved shape to conform to the generally curved top surface of a human foot. If we look at the cross-sectional area of the foot coil 10 having a bottom portion of the wire 17B with a top portion of the coil turn wire 17T we see that the area of that turn of the coil wires 14 is decidedly less than the area of the turn of the coil with a bottom wire 18B and a top portion wire 18T. This increasing cross-sectional area is another unique feature of the design of the coil 10 which is that the area of each successive coil around the foot increases in area as one moves from the toe to the ankle. None of the Burnett et al references has any coil with series of straight wires connected to a series of curved wires nor does any Burnett et al have a coil with an increasing inside area as one moves from the toe toward the ankle of a shoe-shaped coil design.

As seen in FIG. 3, the cross section of the wire could be square (FIG. 3A) square but hollow (FIG. 3B) round (FIG. 3C) round with a hollow interior (FIG. 3D) rectangular (FIG. 3E) and rectangular with a hollow interior (FIG. 3F). Either gas or a liquid such as water could be made to flow through any one of the hollow wires in order to either heat or cool the wire to provide additional comfort for a patient that is using the shoe-shaped coil to relieve foot and ankle pain.

Figure 4:
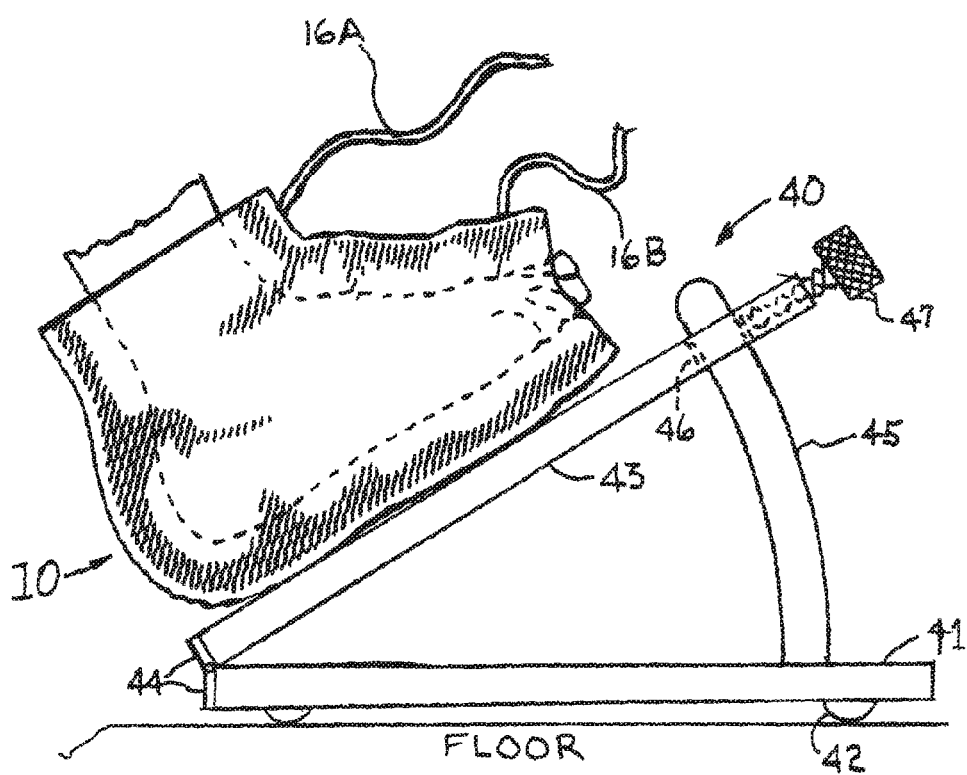
FIG. 4 is a side view of an adjustable angle foot platform.
Figure 5:
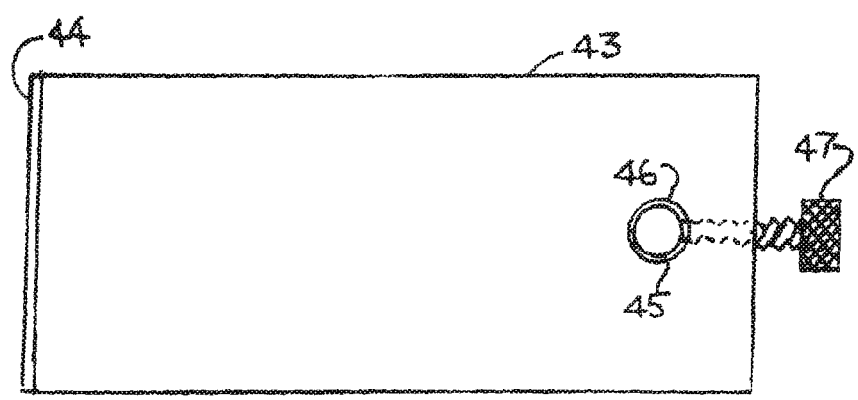
FIG. 5 is a top view of the adjustable angle foot platform of FIG. 4.

FIG. 4 is a side view and FIG. 5 is a top view of an adjustable tilt table 40 onto which the shoe-shaped coil 10 can be placed by the patient. The tilt table 40 has a bottom platform 41 with four rubber or plastic buttons 42 underneath for preventing the tilt table 40 from sliding on the floor. The top platform 43 has a hinge 44 that attaches it to the bottom platform 41. The top platform 43 also has a hole 46 through which can slide a round, curved metal cylinder 45 which is used to adjust the angle "a" of the top platform 43 relative to the bottom platform 41. The knurled handled screw 47 can be loosened to adjust the angle "a" of the top platform 43 and can then be tightened to hold that angle fixed relative to the bottom platform 41. By this means, the coil system 10 that is connected by the wires 16A and 16B to the pulse generator (not shown) can be adjusted for the optimum comfort of the patient as he/she undergoes a somewhat lengthy procedure for the treatment of foot and ankle pain.

For some patients, getting their painful foot into the sneaker-shaped coil shown in FIGS. 1 and 2 can be a significant problem. That large a coil also has a significantly higher electrical resistance and inductive reactance that can limit the electrical current pulses passing through it as compared to a lower resistance and lowered inductive reactance as would be the case for each one of the three separately activated coils 51, 52 and 53 as shown in FIG. 6. Therefore, when actuated separately, each of the coils 51, 52 and 53 can produce a magnetic pulse having a higher intensity as compared to the magnetic pulse intensity that can be achieved with the same pulse generator when used with the single coil of FIGS. 1 and 2.

FIG. 6 illustrates a foot coils system 50 for treating foot pain that utilizes a set of three separate coils; a bottom coil 51, a top coil 52 and a back of the foot and lower ankle coil 53. Each of these coils 51, 52 and 53 would consist of 5 to 25 turns of wire having an AWG rating between 6 and 12. To get these wires to bend most easily, they would optimally be formed from stranded wire that is either with all strands in electrical connection to every other strand or the wire could be Litz wire where every stranded is coated with insulation. It is also possible, but not desirable, to have a solid copper or aluminum wire for each of the three coils. By having three separate coils, each of which could be connected to a pulse generator (not shown) then each coil can be fired sequentially. This sequencing for coil activation overcomes the disadvantage of the single coil design of FIGS. 1 and 2 which design limits the intensity of the magnetic pulses onto the foot and ankle due to the increased electrical resistance and inductive reactance of a single coil that would surround the entire foot and part of the ankle.

In FIG. 6, the shape of the wire coils 51, 52 and 53 are shown from one side of the foot and ankle. It is obvious to a person of ordinary skill in this art that the coils 52 and 53 would have a symmetrical portion on the opposite side of the foot. A plan view of the coil 51 is shown in FIG. 7. Each of these coils 51, 52 and 53 would be encased in a plastic housing (not shown) that would preferably have a strap 54 formed from Velcro (or a similar attachment means) to attach that coil onto the foot and lower portion of the ankle. This could typically be accomplished as follows:

1. The bottom coil 51 is placed under the foot.
2. The top coil 52 is placed on top of the foot.
3. A Velcro (or similar) strap attached to the bottom coil 51 is wrapped around the top of the foot including a portion of the top coil 52.
4. The coil 53 is then placed around the back of the foot and lower portion of the ankle with a Velcro (or similar) strap (not shown) that holds that coil 53 in place. Of course it should be understood that there are a large variety of straps that could be used to secure the three coils 51, 52 and 53 onto the patient's foot and lower ankle.

Each of the coils 51, 52 and 53 can be successively electrically connected to the pulse generator (not shown) in a similar manner as to how the coil 10 shown in FIGS. 1 and 2, or each of the three coils 51, 52 and 53 can be attached at the same time to the pulse generator (not shown). To get the maximum magnetic field into all regions of the foot and lower ankle from a single pulse generator, it is optimum to attach each of the coils 51, 52 and 53 separately and sequentially to the pulse generator.

FIG. 7 is a plan view of the wires of the bottom foot coil 51 showing a shape that is generally in the form of an elongated racetrack. It should be understood that there are multiple turns of the wire and as many as five layers of wires, although two wire layers has been found to be optimum. Other shapes such as a figure eight or having a slightly elevated portion of the coil 51 under the arch of the foot are clearly envisioned. It should be understood that the bottom coil 51 when used by itself would be an optimum means to treat foot pain caused by plantar fasciitis. In that case, only the bottom coil 51 would be used with the strap 54 attaching that coil 51 onto the patient's foot prior to actuation of the pulse generator to produce the desired magnetic pulsations.

It should be understood that a patient having pain in one foot nearly always has a similar level of pain in the other foot. Therefore, after one foot has been treated for pain, it would be typical for the other foot to have a similar treatment.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A magnetic coil and pulse generator system for eliminating or reducing foot pain or both foot and ankle pain of a patient, the system comprising:

an electrical pulse generator for producing a series of electrical current pulses having a peak current pulse amplitude of between 500 to 10,000 Amperes; and a magnetic coil system consisting of three separate magnetic coils including a substantially planar and ovally contoured first coil configured to be contiguous to and positioned under a foot of the patient, a second coil configured to extend over and be contiguous to a top of the foot of the patient, and a third coil configured to be contiguous to and positioned on opposing sides of a lower portion of an ankle of the patient, the electrical pulse generator being electrically and successively connected to the magnetic coil system, the three magnetic coils being sequentially energized by said electrical pulse generator, wherein the magnetic coil and pulse generator system is configured to generate magnetic pulses within the foot and the lower portion of the ankle of the patient, said magnetic pulses having a peak amplitude of at least 0.3 Tesla, said magnetic pulses decreasing or eliminating pain experienced by the patient in the foot and lower portion of the ankle.

2. The system of claim 1 wherein the electrical pulse generator includes controls to adjust a frequency and an amplitude of the electrical current pulses produced by the electrical pulse generator.

3. The system of claim 1 wherein each of the three separate magnetic coils is wound from wires that are rated between 6 and 12 AWG.

4. The system of claim 1 wherein the electrical current pulses created by the electrical pulse generator generate magnetic pulses having a rise time to a point of peak amplitude of the created magnetic field that is between 50 and 500 microseconds.

5. The system of claim 4 wherein the magnetic pulses have a rise time to a point of peak amplitude of the magnetic field of approximately 150±25 microseconds.

6. The system of claim 4 wherein the peak amplitude of the magnetic pulses generated by any one of the three magnetic coils is between 0.5 and 3.0 Tesla.

7. The system of claim 1 wherein the peak electric current pulse produced by the electrical pulse generator is between 2,000 and 10,000 Amperes.

8. The system of claim 1 wherein each of the three magnetic coils has approximately 15±10 turns of an electrically conducting, insulated wire.

9. The system of claim 1 wherein each of the three coils of the magnetic coil system is encased in a plastic material with a means to secure each coil around the foot or around the foot and ankle.

10. The system of claim 9 wherein the means to secure any one of the three magnetic coils to the foot or around the foot and ankle is a Velcro strap.

11. The system of claim 1 wherein of the magnetic coil have a cross section selected from the group of cross-sectional geometries consisting of: square, hollow square, round, hollow round, rectangular, and hollow rectangular.

12. The system of claim 11 wherein the wires for said magnetic coil are formed from either a solid electrical conductor or a multitude of stranded wires with each of the strands being electrically connected to adjacent strands or with each strand being in the form of a Litz wire where each strand is insulated from every other wire strand.

* * * * *